United States Patent [19]

McKay

[11] Patent Number: 5,616,121
[45] Date of Patent: Apr. 1, 1997

[54] METHOD FOR ALLEVIATING PAIN IN A WOUND

[76] Inventor: Douglas W. McKay, 341 Moosa Blvd., Eunice, La. 70535

[21] Appl. No.: 274,763

[22] Filed: Jul. 14, 1994

Related U.S. Application Data

[62] Division of Ser. No. 107,914, Aug. 17, 1993, abandoned.

[51] Int. Cl.$^6$ ..................................................... A61M 1/00
[52] U.S. Cl. .............................. 604/35; 604/28; 604/30; 604/93
[58] Field of Search ................................ 604/27, 28, 35, 604/40, 43, 44, 96, 120, 30, 31, 93; 600/158, 156

[56] References Cited

U.S. PATENT DOCUMENTS

| | | | |
|---|---|---|---|
| 3,771,527 | 11/1973 | Ruisi | 604/96 |
| 4,650,462 | 3/1987 | DeSatnick et al. | 604/30 |
| 4,722,734 | 2/1988 | Kolln | 128/DIG. 12 |
| 4,755,168 | 7/1988 | Romanelli et al. | 604/31 |
| 4,795,424 | 1/1989 | Burner | 604/30 |
| 4,820,265 | 4/1989 | DeSatnick et al. | 604/30 |
| 5,120,312 | 6/1992 | Wigness et al. | 604/93 |

*Primary Examiner*—Robert A. H. Clarke
*Attorney, Agent, or Firm*—Lowe, Price, LeBlanc & Becker

[57] ABSTRACT

An apparatus and method for treatment of a wound with a medicinal solution is disclosed. Generally, the apparatus contains an injection tubing, a suction tubing, and a controller for controlling the opening of the injection tubing and the suction tubing in order to introduce the solution to the wound, and then drain the fluid from the wound area. The controller may contain a first and second valve, as well as a timer that measures predetermined cycles of time.

17 Claims, 2 Drawing Sheets

METHOD FOR ALLEVIATING PAIN IN A WOUND

This is a divisional of application Ser. No. 08/107,914 filed on Aug. 17, 1993, now abandoned.

This invention relates to an apparatus and method of treating wounds. More particularly, but not by way of limitation, this invention relates to an apparatus and method of treating wounds with the use of a suction and irrigation system that utilizes a control means to control injection, injection rates, suction, and suction rates, as well as measuring various time intervals for the diverse treatments.

Open traumatic wound or surgical wounds of the musculoskeletal system are very painful and inflamed. Bleeding in these wounds expands the tissue which leads to a large fluid sac containing blood, extracellular fluid and debris which may form a cyst and need evacuation. The accumulation of this fluid swells and expands the wound causing increasing pain and delayed healing. The accumulation of large fluid sacs of fluid blood debris can lead to infection. The more accumulated material, infection and inflammation leads to increasing scar tissue. The scar tissue in the joints may lead to stiffness and pain of that joint. Scar tissue in muscle and around tendons results in weakness and decreased function.

The state-of-the-art for management of open wounds from injury or surgery in the 19th Century, was to leave the wound open. However, this led to delayed wound closure and delayed recovery and resulted in bad scars. Conventional state-of-the-art is to meticulously control bleeding at the time of surgical intervention. Unfortunately, not all of the small vessels are found and vessels can be in spasm and not bleed until after closure. Also, bone bleeding cannot be controlled by ligature or cautery. Thus, the accumulation of blood in a closed wound of the musculoskeletal system is almost inevitable. Pressure dressings have been used to control bleeding and accumulation of blood in wound but this can lead to pain, delayed healing and thrombophlebitis.

Suction of wounds has been the advancement of the 20th Century to control the accumulation of blood, fluid and debris in wounds. Continuous suction of the wound has various limitations and problems. A limitation is that only a small area of the wound comes in contact with the tube. After removing fluid and blood, suction through a tube with perforations tends to draw in firmer debris, soft tissue, joint linings, muscle tissue, fibrous tissue into the perforations and thereby stops the flow of fluid and blood. Once the fluid and blood flow has stopped, the blood can clot in the perforations and tube preventing further suction from the wound thus allowing accumulation of blood, fluid and debris in the rest of the wound leading to numerous complications and pain.

Stopping the suction, interrupting the closed system and manually irrigating the tube can temporarily restore function. The backflow or irrigation restarts the system but once the system is again in operation the soft tissue gets into the perforations and stops the flow. When the system is interrupted and made open there is the risk of introducing contamination into the wound. In other words, the present state-of-the-art requires the opening of the closed system, manually irrigating the wound and creating a risk of infection with only temporarily reconstitution of the drainage by suction.

Other problems associated with musculoskeletal surgery is that of postoperative pain. The current methods of controlling pain is use of narcotics which is administered by IV therapy, intramuscular therapy or oral therapy. Also, suction of blood and fluid in the wound, as previously described is utilized, in order to prevent inflammation. A regional anesthetic may be employed which means intermittent anesthetic agent injected around a peripheral nerve supplying the area of the body that has an open wound.

A more central control of pain may be utilized by injecting a local anesthetic agent in and around the spinal cord. This process is known as Epidural Analgesia. The anesthetic agents can be administered intermittently or continuously. Also, anti-inflammatory medication, either orally or intramuscular, may be administered for the treatment of pain.

Other problems associated with the treatment of open wounds includes the onset of infection. The care for infection can be an expensive, devastating problem for an open wound, particularly when it occurs in the joints or in the bone. The present state-of-the-art for prevention or control of infection has been aseptic sterile technique in the operating theater. Other methods include meticulous control of wound bleeding. Also, irrigation of the wound with saline and antibiotics before and at the time of closure of the wound has been used to control infection.

The treatment of infection can also be done by debridement of dead soft tissue or debris in the open wound. Also, prophylactic IV antibiotics may be used before, during and following surgery in order control and prevent infection.

The invention presently disclosed solves the above noted problems by diminishing the pain of the patient, diminishing hematoma formation, diminishing development of infection and inflammation, diminishing future scar tissue formation, and decreasing the time of rehabilitation as well as improving overall rehabilitation.

SUMMARY OF THE INVENTION

The present invention contains claims to an apparatus and method of treating a wound with a medicinal solution. The apparatus will generally comprise an infusion tubing means for infusing a prepared solution into the wound of the patient, with the infusion tubing means having a fluid passageway. A suction tubing means for suctioning fluids from the wound of the patient, said suction tubing means having a fluid passageway is also included, as well as control means, operatively connected to the injection tubing means and said suction tubing means, for controlling the fluid passageway of said injection tubing means and said suction tubing means is also included.

The invention will also consist of joinder means for joining the injecting tubing means and the suction tubing means; an in situ tubing having a perforation for communication with said joinder means, with the in situ tubing being located within the wound; and, vacuum means, operatively connected to said suction tubing means, for vacuuming the fluid from the wound.

In one embodiment, the solution infused into the wound may contain comprises a narcotic agent, an anesthetic agent, an anti-inflammatory agent, and an antibiotic.

The apparatus may also comprise a first valve having an open position and a closed position, the valve being operatively connected to the infusion tubing means so that when the valve is in the open position, the solution is in fluid communication with the wound. A first shifting means for shifting the first valve from the open position to the closed position as well as a timer means for timing and then activating the shifting means so the shift means shifts said first valve from the open position to the closed position at preset intervals of time during the infusion, suction, and the bathing modes is also included.

A second valve having an open and closed position may also be included, with the second valve being operatively connected to the suction tubing means so that when the second valve is opened, the fluid in the wound is in communication with the vacuum means so that the fluid can be drained from the wound. The invention may also include a second shifting means for shifting the second valve from open to close or close to open, and wherein the timer means also includes means for timing then activating the second shifting means so that the shift means shifts the second valve from the open position to the closed position at preset intervals of time.

In another embodiment, the control means contains a second valve having an open position and a closed position, the second valve being operatively connected to the suction tubing means so that when the valve is in the open position, the fluid in the wound is in communication with the vacuum means. The control means may also contain a positive pressure pump for injecting into the wound the controlled amount and rate of solution.

A method of treating wounds is also disclosed. Generally, the method comprises the steps of preparing a solution, and then the solution is infused into the wound. After the expiration of a specified time period, the infusion of the solution is interrupted. The length of time the solution is allowed to bathe (i.e. the length of time of the interruption) in the wound is timed by the control means.

The method may further comprise the steps of suctioning the solution from the wound after the expiration of the specified interruption time interval. In other words, the length of time that the wound was bathed in the solution is measured, and after this preset amount of time has passed, the fluid will be drained from the wound. The length of time that the wound is suctioned will also be timed, and the suctioning will be stopped after the expiration of a specified time period that the wound was being evacuated.

The method may further comprise the steps of timing the duration of the interruption from the point where the suction is stopped; thereafter, the next time interval is measured, and after expiration of a preset period of time, the solution is again infused into the wound. The time of infusion is also measured, and the infusion is interrupted after the expiration of a preset timed interval, thus allowing the wound to bathe in the solution.

The method further comprises the steps of suctioning the solution from the wound after the expiration of a preset timed interruption interval. The duration of the suctioning is also timed, and the suctioning will be discontinued after the expiration of the timed suctioning interval.

In practicing the method of this invention, the step of preparing the solution includes providing a medicinal solution which may be anesthetic agent, narcotic agent, antibiotic, antiseptic agent and anti-inflammatory agent. The solution is injected into the wound at a predetermined amount, rate and time.

A feature of the present invention includes the use of the control means for controlling both the infusion tubing and the suction tubing fluid passageways. Another feature is use of the timing means, operatively associated with the control means, for timing the intervals of infusion of the solution, intervals of bathing the solution in the wound, and intervals of suctioning the fluid from the wound area.

Another feature of the invention includes use of an in situ tubing, in the wound area, which will serve as a conduit for the passage of the infusion fluid into the wound, as well as a conduit for the fluid that is drained from the wound during suctioning. Yet another feature is the perforations located on the in situ tubing that allows for passage of the solution, as well as drainage of fluid from the wound.

Still yet another feature includes the use of a first valve, operatively associated with the infusion tubing means, that when open allows for the infusion solution to feed into the wound. Yet another feature includes the use of a second valve having an open position and a closed position, with the second valve being operatively connected to the suction tubing means so that when the valve is in the open position, the fluid in the wound is in communication with the vacuum means so that the fluid can be evacuated from the wound.

Another feature of the invention includes the use of a solution that may contain a narcotic agent, an anesthetic agent, and anti-inflammatory agent, and/or an antibiotic depending on the particular needs of the patient. The agents may be infused together, or in varying degrees in series to one another.

An advantage of the present invention includes the ability to diminish pain by the infusion of a local anesthetic agent into the operative site of the musculoskeletal system wound whether it is a joint, adjacent to a fractured bone, injury to or operated on soft tissue, muscles, reconstructed extremity or back surgery.

Another advantage is that the invention diminishes infection by having in the infusion solution antibiotics which will be directly injected through the tube into the joint or musculoskeletal wound. Also, periodic evacuation of blood, fluid and solution diminishes the chance of infection.

Yet another advantage is that the method and apparatus of the present disclosure will diminish inflammation by evacuating blood and fluid from the inflamed wound. The solution used in this invention may contain an anti-inflammatory agent to decrease inflammation. Diminishing inflammation will improve and decrease time of rehabilitation of the patient. The major benefit of decreasing inflammation is decreasing scar tissue and diminishing stiffness and poor function of the extremity.

DESCRIPTION OF THE PREFERRED EMBODIMENTS

Figure 1:
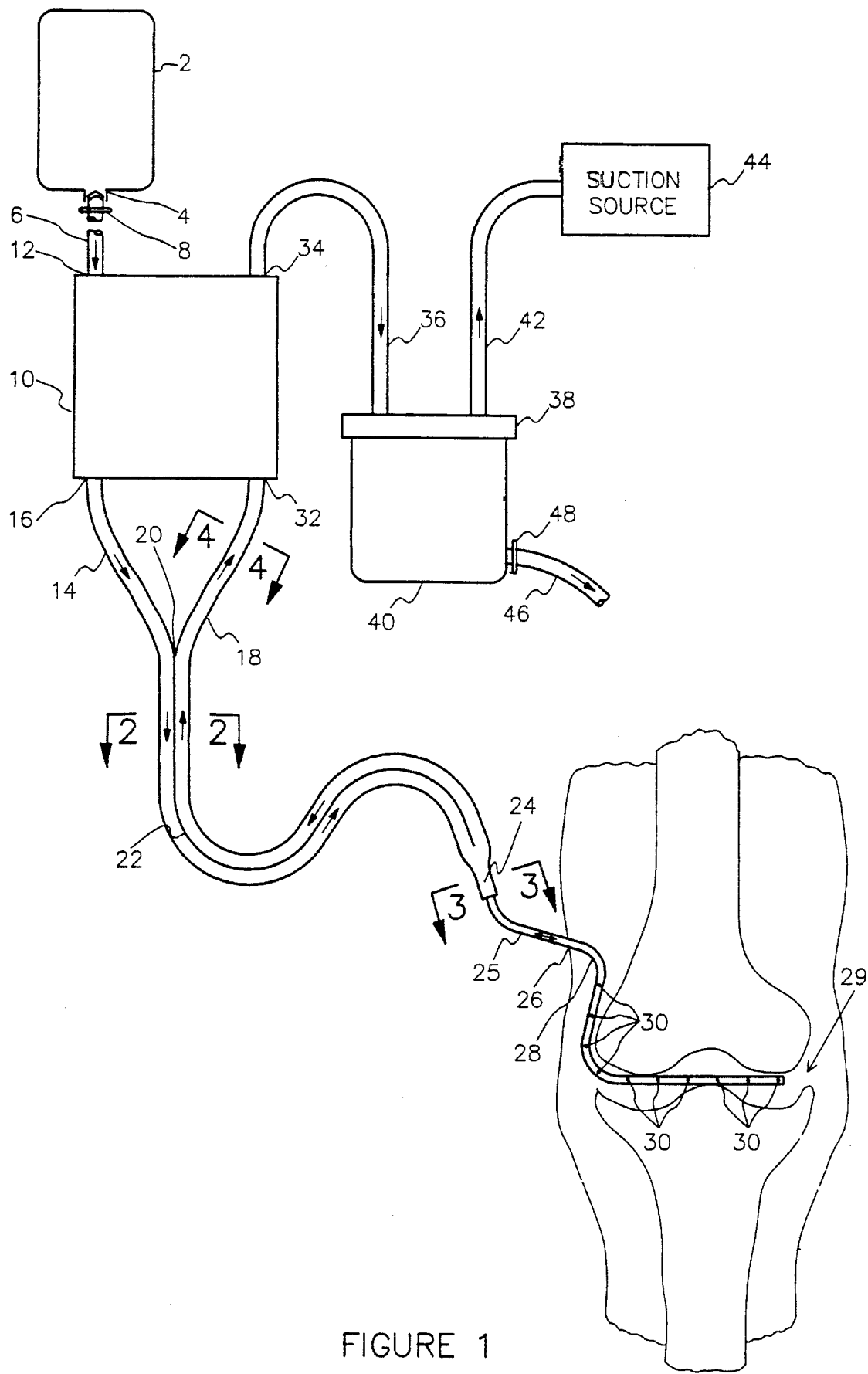
FIG. 1 is a perspective illustration of the apparatus as applied to a patient.

Referring to FIG. 1, a perspective illustration of the apparatus is shown. The IV bag 2 will contain a solution such as a narcotic agent, an anesthetic agent, an anti-inflammatory and/or antibiotic, depending on the needs of the particular patient. The bag 2 will have attached thereto a connector 4 that will connect the bag with a first section of the infusion tubing 6 that has a passageway therein to convey the solution.

The tubing 6 will have disposed thereabout a shut-off valve member 8 that is capable of closing the passageway of tubing 6 to flow. The tubing 6 will in turn lead to the control box means 10 for controlling the fluid passageway of the tubing 6, as well as the suction tubing which will be described herein. The tubing 6 will be connected to the control means 10 at point 12.

Figure 2:
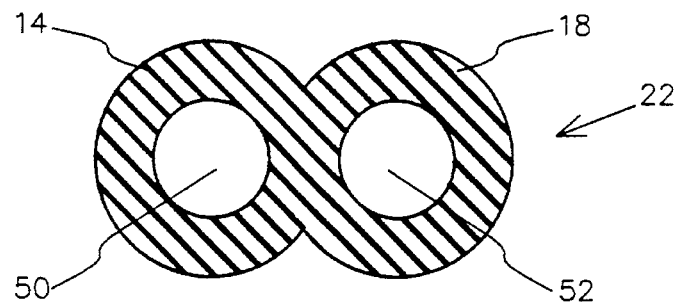
FIG. 2 is a vertical cross-section view of a section of joined tubing.
Figure 3:
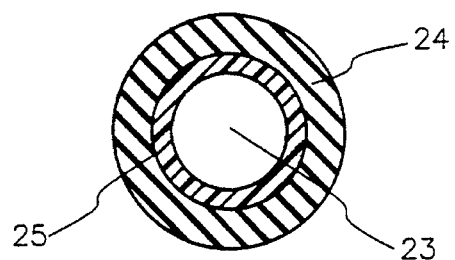
FIG. 3 is a vertical cross-section view of the joinder tubing.

Affixed to the control means will be the second section of the infusion tubing 14, with the second section of the infusion tubing 14 be attached to the control box at 16. The infusion tubing will be attached to the suction tubing 18 at point 20 and will thus form a joint tube 22 that has two separate passageways, as seen in FIG. 2. Then, the joint tube 22 will converge such that there will be one central passageway 23, as seen in FIG. 3. Thus, the joinder portion 24 of the joint tube allows for a central passageway for the infused solution, as well as the fluid which is drained from the wound area 29.

Disposed within as well as extending from the joint tube 22 will be a single in situ tube 25, that is preferably made of clear, synthetic plastic. The in situ tube 25 will have passageway 23 disposed within its inner diameter. The in situ tubing 25 will have thereon a mark 26 at the point where the tube 25 enters the skin of the patient so that personnel can determine whether the tubing is in the proper place. The tubing 24 will have a portion that is smooth, represented by the numeral 28, which is in the entrance to the wound area 29, which in FIG. 1 is the knee where it enters into the synovium cavity as depicted in FIG. 1.

The in situ tubing 25 is made out of a synthetic plastic material which is flexible, clear, soft but will recoil to its original shape. A portion of the tube 25 in the wound 29 has perforations 30 through the sidewalls at various, appropriately placed sites. The material of the tube can be sterilized and yet not lose its strength and physical characteristics. The size of the tube may be between 5.0 and 12.00 mm. The reason for using one tube in the wound in the preferred embodiment is to keep the tube 25 and perforations 30 open for the infusion and suction cycles. The solution at the beginning of the infusion cycle opens up the tube and the perforations and floats the soft tissue away from the tube 25. In one embodiment, the length of the tubing may be approximately 28 inches from the control means 10 to the wound area 29, depending on the length of the wound. The amount of perforated tube will be approximately 12 inches and can be cut to length. The tube 28, the smooth portion, from the perforation may be approximately 16 inches depending on individual circumstances.

The perforations 30 are situated on the in situ tubing 24. The perforations will allow communication from the passageway of the in situ tubing 24 to the wound area 29, and this is true regardless if the solution is being infused into the wound or if the fluid is being drained from the wound.

The suction tubing 18 will be attached to the suction inlet 32 of the control means 10. Extending from the control means 10 from the suction outlet 34 of the control means 10 is the second section of the suction tubing 36, with the suction tubing 36 being connected to the cap member 38 of the evacuation reservoir 40. As seen in FIG. 1, the cap member 38 will also have associated therewith a main suction line 42 which in turn will be connected with a suction source 44 that in a typical hospital can be a pump located in the wall, or alternatively, some other source to create a pressure differential. Also, leading out from the evacuation reservoir 40 is the drainage tubing 46 that is used to drain the contents of the evacuation reservoir 40. The drainage tubing 46 will have associated therewith a clamp valve 48 that serves to open and close the passageway of the drainage tubing 46.

Figure 4:
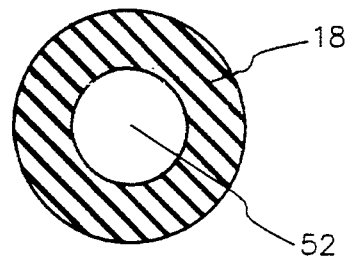
FIGS. 4 is a vertical cross-section views of a section of suction tubing.

Referring to FIG. 2, a cross-section taken along line 2—2 depicts the infusion tubing 14 and the suction tubing 18 joint together along with the passageway 50 of the infusion tubing, and the passageway 52 of the suction tubing. FIG. 3, which is a cross-section taken along line 3—3 depicts the joinder tubing 24 with the in situ tubing 25 being disposed within the joinder tubing's 24 inner diameter. Finally, in FIG. 4, the suction tubing 18, with the inner diameter passageway 52 is illustrated.

Referring again to FIG. 1, the control means 10, which in the preferred embodiment is a mechanical device that is either electrically or battery operated, will have a first valve means for opening and closing the passageway 50 of the infusion tubing 14, second valve means for opening and closing the passageway 52 of the suction tubing 18. Also, a timer means is included for timing the length of time of an infusion cycle or suction cycle, or alternatively for timing a cycle that both passageway's 50, 52 are closed. The control means will also have a first shifting means that will cause the first valve to shift from the open to the close position (or from the close to the open position) upon the expiration of a predetermined amount of time, as well as second shifting means that will cause the second valve to shift from open to the close position (or from the close to the open position) upon the expiration of a predetermined amount of time.

The previously mentioned timer means will also measure the period of time during which the suction tubing 18 passageway is opened so that fluid from the wound area 29 is being drained, as well as measuring the time period that the suction line is closed. The shifting means will also cause the second valve means from either the closed position to the open position, or alternatively, from the open position to the closed position, depending on the particular time cycle.

The control means will also have means for varying the amount of solution that is being infused into the wound area 29, therefore, the rate of infusion can vary at the discretion of the operator. The control means may also include a positive pressure pump for injecting into the wound the pre-determined quantity and rate of the medicinal solution into the wound area 29.

OPERATION

The specific type of solution, or solutions, will first be prepared. In a typical operation, a medicinal solution is infused for a prescribed amount, rate and time. The treating physician has great discretion as to the exact type of solution, the amount, rate and time of infusion and bathing times. The control means may have a control as to the specific quantity to be infused as well as a control means for controlling the rate of infusion and period of time.

The timer means has been measuring the length of time of the infusion. Also, during this period, the suction or vacuum side has been closed via the second valve being in a closed position. After the predetermined length of time of infusion, the first valve member will shift to a closed position whereby the infusion tubing will now be closed.

For a preset timed period, the solution bathes the wound. The delay after this infusion but before evacuation is to allow the solution to circulate in the wound prior to evacuation. After expiration of this time, the suction tubing will be opened by the shifting of the second valve into the open position thereby opening the passageway 52 to the suction source 44. The suction tubing 18 will be opened for a calibrated amount of time. Following the specified amount of time that the wound area 29 is suctioned, the suction tubing 18 is shut-off via the second valve closing. At this point, the entire cycle can be repeated starting again with the opening of the first valve thereby opening the infusion tubing. It should also be noted that the control means may also contain a separate program so that during the 8 hours of sleep, or other patient care as needed, the amount of infusion can be decreased or increased if necessary for patient comfort.

A typical operation of the method of the invention includes having the control means opening the first valve at 8:00 A.M. thereby allowing infusion of a predetermined amount of solution into the wound. The control means injects at different rates and prescribed amount of solution and prescribed time all of which can be preset at the discretion of the operator. The initial infusion could be set for 50 minutes. Therefore, at 8:50 A.M. the solution stops. Then, there may be a delay of 50 minutes controlled by the control means for a specified amount of time. Thus, at 9:40 A.M., after the delay (and during which the wound was being bathed by the solution) the second valve is opened up thereby allowing the suction tubing to be opened in order to evacuate the blood, fluid, and solution from the wound 29. The predetermined period of time for suctioning can be set at 20 minutes. Therefore, the second valve is shifted to the closed position at 10:00 A.M.

At 10:00 A.M. the cycle would start again which means that the first valve is shifted to the open position and the infusion starts again. The cycles can be repeated, or alternatively, interrupted based on particular patient needs.

Changes and modifications in the specifically described embodiments can be carried out without departing from the scope of the invention which is intended to be limited only by the scope of the appended claims.

I claim:

1. A method of alleviating pain in a body joint subsequent to surgical invasion, which method comprises:
   preparing a solution;
   infusing the solution into the joint;
   timing the interval of infusion;
   interrupting infusion after the expiration of a preset timed infusion interval;
   timing the interval of interruption;
   suctioning the solution from the joint after the expiration of a preset timed interruption interval;
   timing the interval of suctioning;
   interrupting the suction after the expiration of a preset timed suctioning interval.

2. The method of claim 1, further comprising the steps of:
   timing the interval of interruption from the suctioning;
   infusing the solution into the joint after the expiration of a preset timed interruption interval;
   timing the interval of infusion;
   interrupting the injection after the expiration of the timed interval;
   timing the interval of interruption.

3. The method of claim 2, further comprising the steps of:
   suctioning the solution from the joint after the expiration of the timed interruption interval;
   timing the interval of suctioning;
   interrupting the suction after the expiration of a preset timed suctioning interval.

4. The method of claim 1, wherein the solution includes one or more components selected from the group of:
   a narcotic agent;
   an anesthetic agent;
   an anti-inflammatory; and
   an antibiotic;
   and, the step of infusing the solution in the joint includes:
   infusing the solution at a predetermined rate into the joint; and
   measuring the amount of the solution infused.

5. The method of claim 1, wherein infusing is performed at varying rates of infusion, and wherein the preset timed infusion interval is adjusted according to patient need.

6. The method according to claim 1, wherein the steps of infusing, timing the interval of infusion, interrupting the injection, timing the interval or interruption, timing the interval of suctioning and interrupting suctioning are repeated a plurality of times.

7. The method according to claim 1, wherein the joint is a knee.

8. The method according to claim 1, further comprising:
   inserting a tube in the joint;
   infusing the solution into the joint through the tube; and
   suctioning the solution from the joint through the same tube.

9. A method of alleviating pain in a body joint subsequent to surgical invasion, which method comprises:
   preparing a solution;
   infusing the solution into the joint at controlled rate;
   periodically varying the rate of infusion; and
   periodically suctioning the solution from the joint for preset timed intervals.

10. The method according to claim 9, wherein the joint is a knee.

11. A method comprising:
    performing a surgical procedure on a body joint whereby a surgical wound is created;
    inserting at least one tube in the joint;
    closing the surgical wound; and
    alleviating pain in the joint by:
    infusing a solution into the joint through one tube;
    timing the interval of infusion;
    interrupting infusion after the expiration of a preset timed infusion interval;
    timing the interval of interruption;
    suctioning the solution from the joint through said one tube or a second tube after the expiration of a preset timed interruption interval;
    timing the interval of suctioning; and
    interrupting suctioning after the expiration of a preset timed suctioning interval.

12. The method according to claim 11, wherein infusion, timing the interval of infusion, interrupting infusion, timing the interval of interruption, suctioning, timing the interval of suctioning and interrupting suctioning are repeated a plurality of times.

13. The method according to claim 11, wherein the joint is a knee.

14. The method according to claim 11, wherein the solution is infused and suctioned through the same tube.

15. A method comprising:

performing a surgical procedure on a body joint, whereby a surgical wound is created;

inserting at least one tube in the joint;

closing the surgical wound; and alleviating pain in the joint by:

infusing a solution into the joint through one tube at a controlled rate;

periodically varying the rate of infusion; and periodically suctioning the solution from the joint through said one tube or a second tube for preset timed intervals.

16. The method according to claim 15, wherein the joint is a knee.

17. The method according to claim 15, wherein the solution is infused and suctioned through the same tube.

* * * * *